(12) United States Patent
Bronkalla et al.

(10) Patent No.: US 11,449,986 B2
(45) Date of Patent: Sep. 20, 2022

(54) ENHANCING MEDICAL IMAGING WORKFLOWS USING ARTIFICIAL INTELLIGENCE

(71) Applicant: INTERNATIONAL BUSINESS MACHINES CORPORATION, Armonk, NY (US)

(72) Inventors: Mark D. Bronkalla, Waukesha, WI (US); Grant Covell, Belmont, MA (US); Amanda Long, Acton, MA (US); David Richmond, Newton, MA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 1003 days.

(21) Appl. No.: 16/168,281

(22) Filed: Oct. 23, 2018

(65) Prior Publication Data
US 2020/0126215 A1 Apr. 23, 2020

(51) Int. Cl.
| G06T 7/00 | (2017.01) |
| A61B 5/00 | (2006.01) |
| G16H 30/20 | (2018.01) |
| G16H 30/40 | (2018.01) |
| G06N 20/00 | (2019.01) |
| G06N 5/02 | (2006.01) |

(52) U.S. Cl.
CPC .......... *G06T 7/0012* (2013.01); *A61B 5/0013* (2013.01); *G06N 20/00* (2019.01); *G16H 30/20* (2018.01); *G16H 30/40* (2018.01); *A61B 5/0044* (2013.01); *A61B 2576/023* (2013.01); *G06N 5/022* (2013.01); *G06T 2207/30004* (2013.01)

(58) Field of Classification Search
CPC ......... G06T 7/0012; G06T 2207/30004; A61B 5/0013; A61B 5/0044; A61B 2576/023; A61B 6/5217; A61B 2576/00; G06N 20/00; G06N 5/022; G06N 5/046; G16H 30/20; G16H 30/40; G16H 40/20
See application file for complete search history.

(56) References Cited

U.S. PATENT DOCUMENTS

| 5,535,322 A | 7/1996 | Hecht | |
| 6,574,629 B1* | 6/2003 | Cooke, Jr. | ............... G06F 16/40 |
| 7,411,693 B2 | 8/2008 | Loukipoudis et al. | |

(Continued)

*Primary Examiner* — Amara Abdi
(74) *Attorney, Agent, or Firm* — Michael Best & Friedrich +LLP

(57) ABSTRACT

Systems and methods for selectively processing image studies with an artificial intelligence system. One system includes an electronic processor configured to select an image study awaiting review and update a workflow status of the image study to a first status indicating that the image study has been claimed for review by the artificial intelligence system. The electronic processor is also configured to apply at least one of the plurality of rules to the image study to determine whether the image study is applicable for processing by the artificial intelligence system, and, in response to determining the image study is not applicable for processing by the artificial intelligence system based on the at least one of the plurality of rules, update the workflow status associated with the image study to a second status to make the image study available for claiming by a manual reviewer or another artificial intelligence system.

20 Claims, 3 Drawing Sheets

(56) References Cited

U.S. PATENT DOCUMENTS

| | | | |
|---|---|---|---|
| 8,296,247 B2 | 10/2012 | Zhang et al. | |
| 2003/0045958 A1 | 3/2003 | Brandt et al. | |
| 2008/0140723 A1* | 6/2008 | Hernandez | G16H 30/20 |
| 2008/0168107 A1 | 7/2008 | Parvatikar et al. | |
| 2008/0172249 A1* | 7/2008 | Glaser-Seidnitzer | G16H 30/40 |
| | | | 705/2 |
| 2013/0129165 A1* | 5/2013 | Dekel | G16H 30/20 |
| | | | 382/128 |
| 2016/0350919 A1* | 12/2016 | Steigauf | G06V 10/451 |
| 2018/0137244 A1* | 5/2018 | Sorenson | G16H 30/40 |
| 2018/0329609 A1* | 11/2018 | De Swarte | G06T 17/10 |
| 2019/0156947 A1* | 5/2019 | Nakamura | G16H 50/20 |

\* cited by examiner

ENHANCING MEDICAL IMAGING WORKFLOWS USING ARTIFICIAL INTELLIGENCE

FIELD

Embodiments described herein relate to selectively processing image studies with an artificial intelligence system.

SUMMARY

Artificial intelligence ("AI") systems that can process medical imaging studies have become feasible. The results of the AI systems processing the studies can be inserted into workflows for physicians or other medical professionals that utilize medical imaging studies.

For example, workflows (defined organization structures) may be used to track image studies that a user (for example, a physician) is interested in reviewing and analyzing. In response to a physician selecting an image study from the worklist, a Picture Archiving and Communication System ("PACS") viewer may display one or more of the images included in the selected image study and may reserve or pull the image study from a queue of studies awaiting reading or diagnosis.

When a physician reviews an imaging study, the physician may also review an output of an AI system inserted into the workflow. In some instances, the radiologist may wish to wait until the AI system (or multiple AI systems) finishes processing the image study and inserting outputs into the workflow before continuing his or her review of the study.

In other instances, the AI system may actually be performing a "read" of the image study (for example, taking over at least a portion of a review of the image study from the physician and supplementing a diagnosis or other conclusion). In these instances, conflicts arise when the physician attempts to open a study that is currently being reviewed by the AI system(s). These conflicts may include waste of resources, billing conflicts, and double reads that produce conflicting opinions.

Furthermore, AI systems tend to be computationally-intense by requiring a large amount of processing power, memory, or other computing resources. Accordingly, optimizing AI systems to maximize the number of studies analyzed, determine whether a specific image study should be excluded from AI review, or whether all AI systems that are applicable to a current image study are running at capacity and are therefore unable to process more studies makes efficient use of AI systems within a reading workflow.

To meet these opposing needs and to enhance the use of AI systems in the reading workflow, embodiments described herein provide systems and methods for selectively processing image studies with an artificial intelligence system. The systems and methods allow AI systems to claim image studies for review, reject studies or revert a previously claimed study when the AI system cannot process the study in a timely manner, and report on the status of the AI system processing the image study. Note that there may be multiple steps in the AI processing system and multiple opportunities to release the claim on a study so that the study can be released to the physicians (manual) work queue as early as possible and with the use of the least possible computing resources. This allows a reviewer, such as a physician, to coordinate workflows between herself or himself and one or more AI systems, which saves review time for the reviewer and efficiently utilizes available computing resources.

For example, one embodiment of the invention provides a system for selectively processing image studies with an artificial intelligence system. The system includes a non-transitory computer-readable medium storing a plurality of inclusion rules, the plurality of inclusion rules related to an applicability of an image study for processing by the artificial intelligence system, and an electronic processor. The electronic processor is configured to access a plurality of image studies awaiting review, select one of the plurality of image studies and update a workflow status associated with the selected one of the plurality of image studies to a first status indicating that the one of the plurality of image studies has been claimed for review by the artificial intelligence system, and apply at least one of the plurality of inclusion rules to the selected one of the plurality of image studies to determine whether the selected one of the plurality of image studies is applicable for processing by the artificial intelligence system. The electronic processor is also configured to, in response to determining the selected one of the plurality of image studies is applicable for processing by the artificial intelligence system based on the at least one of the plurality of inclusion rules, process the image study with the artificial intelligence system. In addition, the electronic processor is configured to, in response to determining the selected one of the plurality of image studies is not applicable for processing by the artificial intelligence system based on the at least one of the plurality of inclusion rules, update the workflow status associated with the selected one of the plurality of image studies to a second status to make the selected one of the plurality of images studies available for claiming by a manual reviewer or another artificial intelligence system.

Another embodiment provides a method for selectively processing image studies with an artificial intelligence system. The method includes, accessing a plurality of image studies awaiting review, selecting one of the plurality of image studies, and updating the workflow status associated with the selected one of the plurality of image studies to a first status indicating that the one of the plurality of image studies has been claimed for review by the artificial intelligence system. The method also includes, applying, with an electronic processor, at least one of a plurality of exclusion rules to the selected one of the plurality of image studies to determine whether the selected one of the plurality of image studies is applicable for processing by an artificial intelligence system. In addition, the method includes, in response to determining the selected one of the plurality of image studies is applicable for processing by the artificial intelligence system based on the at least one of the plurality of exclusion rules, processing the image study with the artificial intelligence system. Furthermore, the method includes, in response to determining the selected one of the plurality of image studies is not applicable for processing by the artificial intelligence system based on the at least one of the plurality of exclusion rules, updating the workflow status associated with the selected one of the plurality of image studies to a second status to make the selected one of the plurality of images studies available for claiming by a manual reviewer or another artificial intelligence system.

A further embodiment provides a non-transitory, computer-readable medium comprising instructions that, when executed by an electronic processor, perform a set of functions. The set of functions includes accessing a plurality of image studies awaiting review, selecting one of the plurality of image studies, and updating the workflow status associated with the selected one of the plurality of image studies to a first status. The set of functions also includes applying at least one of a plurality of inclusion rules and at least one of a plurality of exclusion rules to the selected one of the plurality of image studies to determine whether the selected one of the plurality of image studies is applicable for processing by the artificial intelligence system and, in response to determining the selected one of the plurality of image studies is applicable for processing by the artificial intelligence system based on the at least one of the plurality of inclusion rules and the at least one of the plurality of exclusion rules, processing the image study with the artificial intelligence system. The set of functions further includes, in response to determining the selected one of the plurality of image studies is not applicable for processing by the artificial intelligence system based on the at least one of the plurality of inclusion rules and the at least one of the plurality of exclusion rules, updating the workflow status associated with the selected one of the plurality of image studies to a second status to make the selected one of the plurality of images studies available for claiming by a manual reviewer or another artificial intelligence system.

Other aspects of the invention will become apparent by consideration of the detailed description and accompanying drawings.

DETAILED DESCRIPTION

Before embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (for example, stored on non-transitory computer-readable medium) executable by one or more processors. As such, it should be noted that a plurality of hardware and software based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (for example, a system bus) connecting the components.

Figure 1:
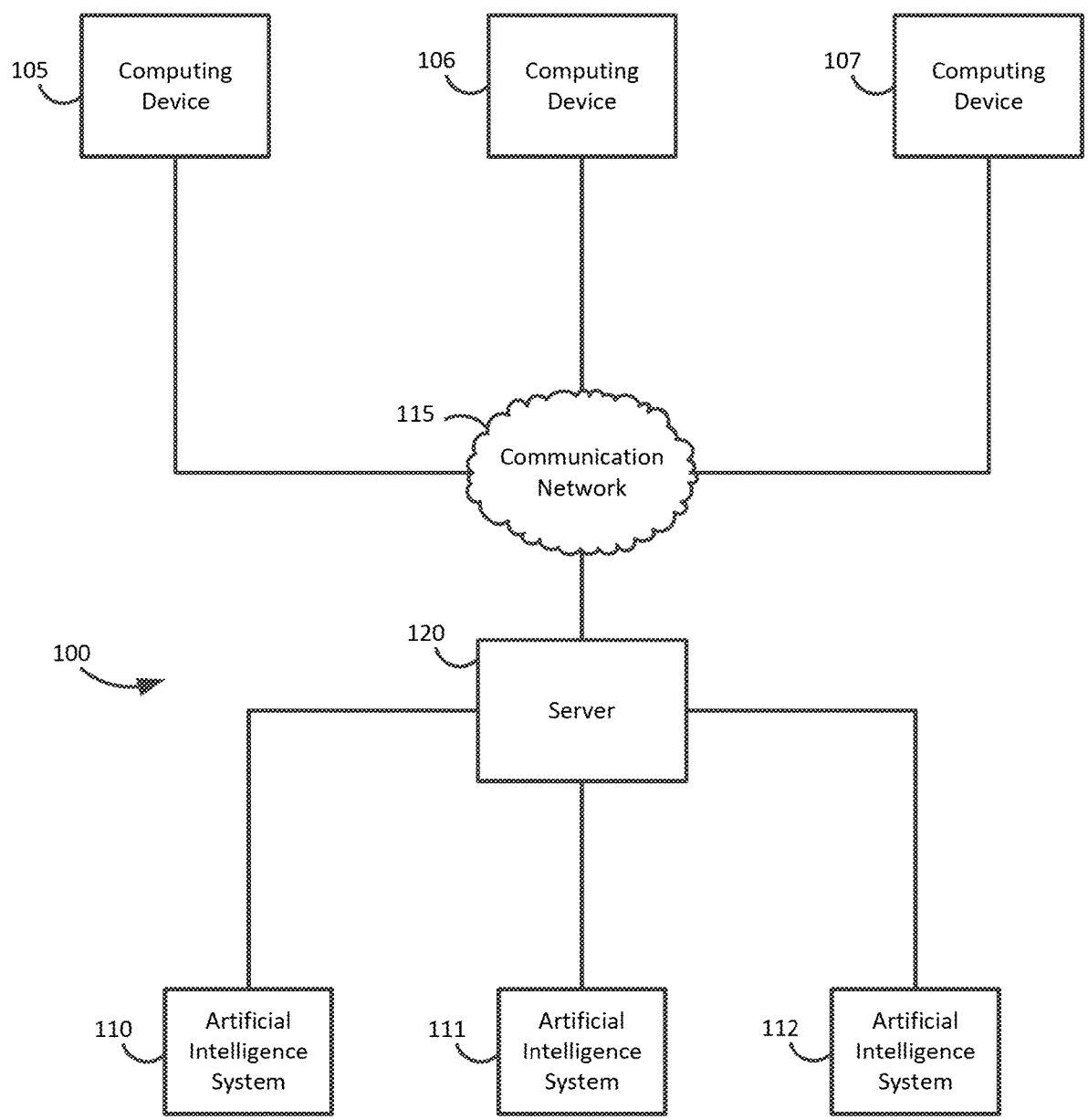
FIG. 1 illustrates a system for selectively processing image studies by an artificial intelligence system according to one embodiment.

FIG. 1 illustrates a system 100 for selectively processing image studies by an artificial intelligence system. The system 100 includes one or more computing devices 105-107 (hereinafter referred to individually as a "computing device 105"), one or more artificial intelligence ("AI") systems 110-112 (hereinafter referred to individually as an "AI system 110"), and a server 120. The computing devices 105-107 communicate with the server 120 via a communication network 115. The communication network 115 includes a wired network, a wireless network, or a combination thereof. For example, in some embodiments, the communication network 115 includes the Internet, a clinical messaging network, a local area network, or the like. As illustrated in FIG. 1, the server 120 communicates with the AI systems 110-112. In some embodiments, the server 120 communicates with the AI systems 110-112 over the communication network 115. In other embodiments, the server 120 communicates with the AI systems 110-112 over one or more separate communication networks.

It should be understood that the system 100 may include any number of computing devices and three computing devices are illustrated in FIG. 1 purely for illustrative purposes. Similarly, the system 100 can include any number of AI systems and three AI systems are illustrated in FIG. 1 purely for illustrative purposes. Furthermore, the functionality described herein as being performed by the server 120 may be distributed over multiple devices, such as multiple servers operating in a cloud environment. In addition, in some embodiments, one or more of the AI systems may be included in the server 120.

Each computing device 105 may be a laptop computer, a desktop computer, a smartphone, a smart wearable device, a tablet computer, and the like. In general, the computing device 105 includes one or more electronic processors, one or more input-output interfaces, and one or more non-transitory, computer-readable memories. As described in more detail below, each computing device 105 may be used by a user, such as a radiologist, physician, or the like, to read image studies, such as performing a manual review or diagnostic of an image study or reviewing the results of a review performed by a separate user or one of the AI systems 110-112.

Each AI system 110 is configured to process medical images and generate various diagnostic outputs. The outputs may include a structured report (including a diagnosis), an annotation, a notification, an alert, or the like. In some embodiments, each AI system 110 is configured to process images generated by predetermined imaging modalities, generated as part of predetermined imaging exam types, generated during a predetermined step in an exam, and the like. When an AI system 110 receives an image that the system 110 is not configured to process, the AI system 110 may simply ignore the image, generate an error, or generate a notification of rejection. For example, when the AI system 110 is configured to read an image study including images of a head where a contrast was used, the AI system 110 may reject a study when contrast was not used. In rejecting a study, the AI system 110 may also perform a selected set of analytics (e.g., a simplified blood-flow analysis instead of a full blood flow analysis) to determine whether the AI system 110 can process the study.

In some embodiments, each AI system 110 maintains a queue of images studies claimed by the AI system 110 for processing. The image studies may be added to or removed from the queue manually by a physician or automatically by a software application (for example, the server 120 as described below). An order of image studies included in the queue may also be manually or automatically updated. After an image study is processed by the AI system 110, the image study is removed from the queue. In some embodiments, an image study can also be removed from the queue when a AI system 110 cannot process it before a turn-around time limit is reached (as described below). As also described below, the queue maintained for an AI system 110 can be used to track a capacity of the AI system 110 to process image studies, which can be used to decide whether to claim the study for processing by the AI system 110.

Each AI system 110 includes one or more software applications that, when executed by an electronic processor, perform one or more artificial intelligence techniques to process an image study. Thus, each AI system 110 may include a server including an electronic processor and non-transitory computer memory storing one or more software applications, wherein the software applications, when executed by the electronic processor, process image studies as described both above and below. It should be understood that in some embodiments, two or more AI systems 110 may be provided via the same server. Furthermore, in some embodiments, an AI system 110 may be distributed over multiple servers, including within a cloud or hybrid cloud environment.

Figure 2:
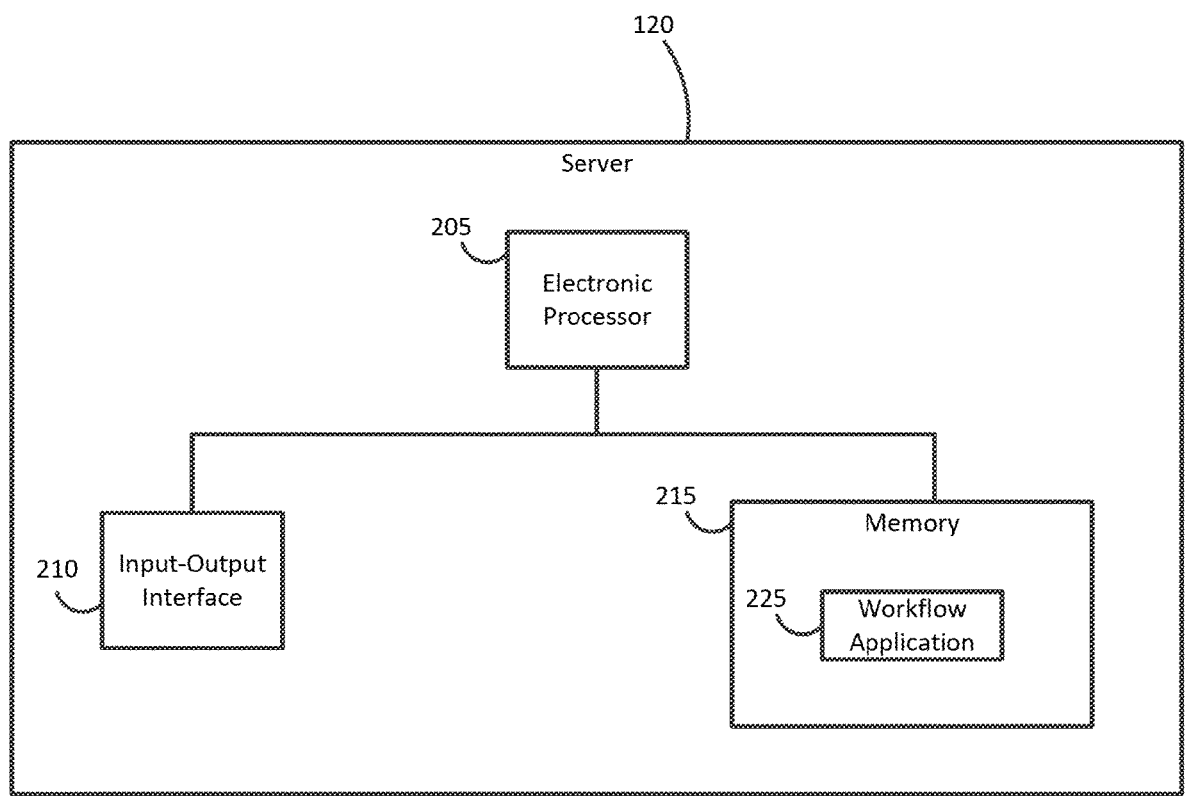
FIG. 2 illustrates a server included in the system of FIG. 1 according to one embodiment.

As illustrated in FIG. 2, in some embodiments, the server 120 includes an electronic processor 205, an input-output interface 210, and a memory 215. The memory 215 includes non-transitory computer-readable memory, such as random access memory, read-only memory, or a combination thereof. The electronic processor 205 can include a microprocessor configured to execute instructions stored in the memory 215. The memory 215 can also store data used with and generated by execution of the instructions. The input-output interface 210 allows the server 120 to communicate with external devices and systems, such as the communication network 115. It should be understood that the sever 120 may include additional components than those listed in FIG. 2 in various configurations. For example, in some embodiments, the server 120 includes a plurality of electronic processors, memory modules, communication interfaces, or a combination thereof. Also, it should be understood that, in some embodiments, the server 120 can performs functionality in addition to the functionality described herein.

In some embodiments, the server 120 is a picture archiving and communication system (PACS). A PACS stores and controls access to electronic medical images generated by one or more imaging modalities (such as computed tomography (CT), x-ray, magnetic resonance imaging (MRI), and the like. In some embodiments, a PACS stores medical image studies in a Digital Imaging and Communications in Medicine (DICOM) format, which may include one or more medical images and associated data, measurements, reports, patient information, and the like. This information may be stored in a DICOM header associated with each image study, each medical image, or a combination thereof. It should be understood that, in some embodiments, the server 120 is separate from a PACS and the server 120 may be configured to communicate with one or more remote PACSs. For example, in some embodiments, the server 120 is separate from a PACS and the separate PACS (or other upstream components) may be configured to apply one or more routing rules similar to the server 120 as described herein. However, in some embodiments, any rules applied by upstream components, such as a PACS, may be coarser (less specific) than the rules described herein as being performed by the server 120. Accordingly, regardless of whether the server 120 includes the PACS or is separate from the PACS, the server 120 is configured to, as described in more detail below, access one or more images stored in a PACS and route images to various destinations, such as a computing device, an AI system, or a combination thereof. It should also be understood that, in some embodiments, the server 120 may be combined with other systems of a healthcare organization, such as a radiology information system (RIS), an electronic medical record (EMR) system, or the like.

As illustrated in FIG. 2, the memory 215 included in the server 120 stores a workflow application 225. The workflow application 225, when executed by the electronic processor 205, is configured to coordinate workflows between a physician and an artificial intelligence system, as described in further detail below. It should be understood that the memory 215 may include other software applications or the workflow application 25 may perform additional functionality not described herein. For example, the memory 215 may include other software applications performing, when executed by the electronic processor 205, productivity functions, such as timekeeping functions, not-taking functions, or the like. Similarly, it should be understood that the computing device 105 may perform at least some of the functionality of the server 120.

Figure 3:
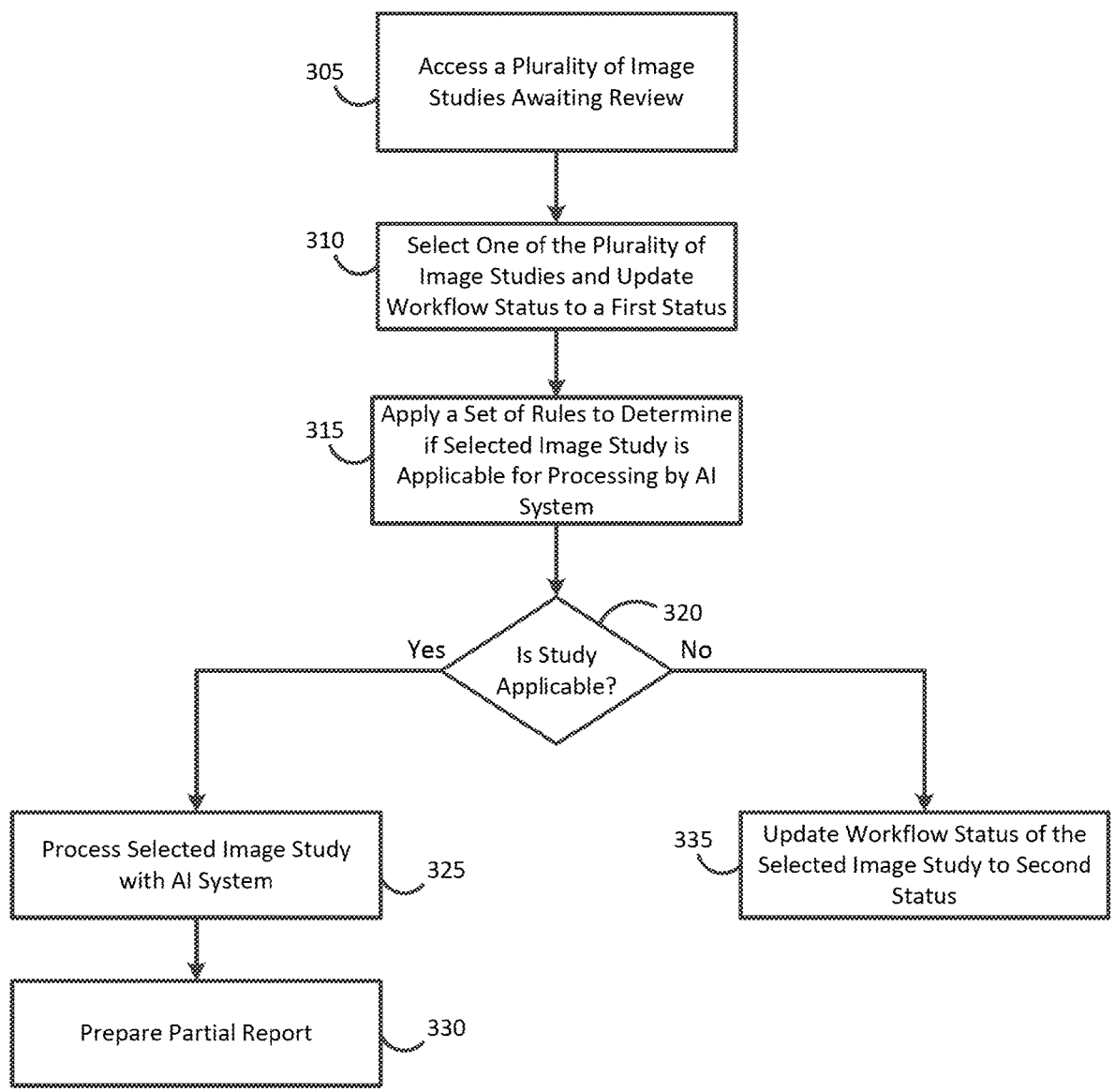
FIG. 3 is a flowchart illustrating a method for selectively processing image studies by an artificial intelligence system performed by the system of FIG. 1 according to one embodiment.

For example, FIG. 3 illustrates a method 300 for selectively processing image studies by the AI system 110 according to one embodiment. The method 300 is described herein as being performed through execution of the workflow application 225 by the electronic processor 205 included in the server 105. However, as noted above, portions of the functionality described herein as being performed by the workflow application 225 may be performed by other applications executed by the server, an AI system, a computing device, or a combination thereof. As illustrated in FIG. 3, the method 300 includes accessing, with the electronic processor 205, a plurality of image studies awaiting review (at block 305). Each of the plurality of image studies includes a plurality of images, and, on some embodiments, each of the plurality of images studies is awaiting review, wherein the PACS or a RIS may manage this workflow and the tracking of image studies awaiting review. For example, the PACS may track a status of each image study stored or managed by the PACS wherein the status indicates whether the image study is awaiting review, has been claimed for review (for example, claimed by a radiologist or claimed by the AI system 110), whether review or "reading" of the image study is in progress or complete, or the like. In some embodiments, the each image study included in the plurality of image studies is similar, such as being related to a specific patient, a specific portion of human anatomy, a specific imaging modality, and the like. Alternatively, the plurality of image studies may be a general collection of image studies to be processed in a healthcare facility, for a specific group of physicians, or the like.

As noted above, each of the plurality of image studies includes a workflow status. The workflow status may be a field of the DICOM header or a separate data field or property associated with an image study. In general, the workflow status indicates a current status or current progress of a review of the image study. The workflow status may have one of a plurality of values, such as "Read," "Processing," "Locked," "Unread, "In Queue," "Claimed," "Assigned," and the like. The workflow status may be changed manually by a physician using the computing device 105 (through selection of an image study for review or completion of a manual review of an image study), changed automatically by the workflow application 225, or changed automatically by the AI system 110 as described below.

As illustrated in FIG. 3, the method 300 also includes selecting, with the electronic processor 205, at least one image study of the plurality of image studies and updating the workflow status of the selected one of the plurality of image studies to a first status (at block 310). The selected image study may include an image study having a workflow status of "Unclaimed," "Unread," "Not Reviewed," or the like. Accordingly, in this way, the electronic processor 205 is only able to select image studies that are not currently in review, image studies that are not currently claimed for review, and image studies that have not already been reviewed.

When the electronic processor 205 selects the selected image study from the plurality of image studies, the electronic processor 205 updates the workflow status of the selected image study to the first status. The first status may be "Claimed," "Processing," "Under Review," "Locked," and the like. In general, the first status indicates to other reviewers and any other AI systems 110 that the selected study cannot be claimed by other reviewers or AI systems 110 (the selected study is locked). Claimed or studies currently being processed may be restricted from access to prevent accidental use. However, in some embodiments, these studies are still generally available for use or viewing with some degree of restrictions or notifications. For example, in some embodiments, to ensure that a study can be viewed as part of urgent care for a patient, claimed and in-process image studies may still be available for viewing.

After the electronic processor 205 selects the selected image study, the electronic processor 205 is configured to apply at least one rule of a set of rules to determine whether the selected image study is applicable for processing by an AI system 110 (at block 315).

The set of rules may include inclusion rules. Generally, inclusion rules can be broad rules that allow for quick determinations of the applicability of the selected image study for processing by a particular AI system 110. For example, one inclusion rule may be that the study must be a screening study. Other inclusion rules may include determining whether the selected study was generated by a predetermined imaging modality that can be processed by an AI system 110. For example, the rules for an AI system 110 may specify that the AI system 110 is only configured to process chest MRI image studies. Similarly, an inclusion rule may determine whether the selected image study has an appropriate number and/or types of images to process (for example, when a study has only 3 images, it may be inefficient to use the AI system 110), whether the selected image study is focused on a predetermined anatomical structure that can be processed by the AI system 110 (for example, the selected image study includes only images of the heart and the AI system 110 is a system configured to process only heart images), or the like. Other inclusion rules may apply to the applicability of AI processing for a particular set of patients (for example, females over the age of 40). The inclusion rules may also determine whether an AI system 110 is running at capacity. For example, as noted above, each AI system 110 may include a queue of image studies yet to be processed. When the queue of an AI system 110 is full (at or above a predetermined number of image studies to be processed), the inclusion rules may specify that the selected image study is not applicable for processing by the AI system 110 due to the amount of image studies in the queue. In some embodiments, the inclusion rules also determine whether a selected image study can be processed in a predetermined amount of time using an AI system 110 to determine whether the study is applicable for the AI system 110. For example, when the rules specify that a turn-around time for reviewing the selected image study will not be met due to the amount of studies in the queue for the AI system, the selected image study may be designated as not applicable for the AI system 110. Accordingly, the inclusion rules can be used to select or claim an image study for processing by an AI system 110 only when the image study can be timely processed by the AI system 110. Thus, the rules may consider the number of items in the queue, a number of minutes of processing represented by the queue (for example, assuming that a predetermined processing time is associated with each item in the queue), a current consumption level of one or more cores, threads, or processing units used by the AI system 110 or a combination thereof to determine whether to process the image study via the AI system 110.

The set of rules may also include exclusion rules. In contrast to inclusion rules, exclusion rules may be narrow and may be designed to reject the selected image study when the selected image study contains characteristics that cannot be processed by the AI system 110. For example, one exclusion rule may reject the selected image study when images in the selected image study contain image artifacts, such as manually-written text, physician comments, and the like. Further examples of exclusion rules may include an exclusion rule that rejects the selected image study when there are patient positioning errors in images, an exclusion rule that rejects image studies where one or more of the images are of poor image quality, an exclusion rule that rejects the selected image study when the AI system 110 is not trained to analyze certain images within the study, an exclusion rule that rejects the selected image study when there is incomplete data (for example, an incomplete DICOM header) or corrupted data, or where there is a minimum data set (for example, a 4-view mammogram or a 2-view chest x-ray), an exclusion rule that rejects the selected image study when any images included in the study contain foreign bodies such as metallic implants such as clips or staples or unrecognized anatomical bodies, an exclusion rule that rejects the selected image study when contrast was not used, and the like. In some embodiments, the exclusion rules include multiple sub-rules and rely on relationships between metadata or low-level, non-computationally intensive analytic processing steps that do not tie up an AI system 110. A claim on an image study can potentially be released at any of these steps to return the study to a physician worklist or queue as quickly as possible and with the least use of computing resources.

It should be understood that the workflow application 225 may be configured to apply one or more inclusion rules, one or more exclusion rules, or a combination thereof to a selected image study. In some embodiments, the rules applied to an image study be relate to an AI system 110 and may define what types of image studies can be processed by the AI system 110 and what types of images studies cannot be processed by the AI system 110. In some embodiments, the workflow application 225 is configured to process image studies for a one AI system 110 and, thus, may apply the same set of rules to each selected image study. However, in other embodiments, the workflow application 225 is configured to not only determine whether a an image study is applicable for a particular AI system 110 but also to identify what AI system 110 of multiple available AI systems 110 is applicable for the image study. Accordingly, after selecting an image study for claiming by an AI system, the workflow application 225 may automatically select an initial AI system 110 for the image study and then apply the rules associated with the selected AI system 110 to the image study. When the rules indicate that the image study is not applicable for the selected AI system 110, the workflow application 225 can select another AI system 110 and repeat this process. In fact, in some embodiments, the results of applying the rules for one AI system 110 may designate a different AI system 110 that may be used to process the image study, and the workflow application 225 may apply the rules for the designated AI system 110 in this situation. It should be understood that the selection and application of rules to apply to a selected image study may be performed by the workflow application 225, the AI system 110, or a combination thereof. For example, by performing this pre-processing at the server 120, the resources associated with the AI system 110 may be used more efficiently and the AI system 110 may be able to generate diagnostic outputs quicker than if the AI system 110 were performing the application of the rules. However, moving some of the rule application to the AI system 110 may make sense to efficiently use functionality included in the AI system 110 for processing an image study. For example, when an AI system 110 performs certain image processing (segmentation or the like) and this functionality is needed to apply one or more rules, using the AI system 110 to apply these rules may be more efficiently than replicating this functionality at the server 120. Accordingly, in some embodiments, the application of the rules may be performed through a combination of processing performed by the server 120 and the AI system 110 to efficiently and effectively determine the proper processing for an image study while minimizing wasted resources.

Based on the results of applying the set of rules to the image study, the workflow application 225 selectively processes the image study with the AI system 110. For example, when the selected image study is determined to not be applicable for processing by the AI system 110 (at block 320), the electronic processor 205 is configured to update the workflow status of the selected image study to a second status (at block 335). In some embodiments, the second status is the same status as the first status. For example, the electronic processor 205 may update the workflow status of the selected image study back to "Unclaimed," "Not Reviewed," "Unread," "Available," or some other workflow status indicating that the selected image study was not processed by the AI system 110 and, thus, is available for claiming by a radiologist or another AI system. In some embodiments, the workflow application 225 updates the workflow status of the returned image study to the status the study had before the image study was selected for potential processing by the workflow application 225. Alternatively, the workflow application 225 may update the workflow status to a particular value to return the image study to the general pool or to a particular destination or pool. For example, the workflow application 225 may assign a particular workflow status that designates that the image study has already been claimed and pre-processed for a particular AI system 110 and was rejected by the system 110 to prevent duplicating this pre-processing or otherwise wasting computing resources.

Updating the workflow status to one of these values may effectively return the image study to a review pool of image studies awaiting reading. Furthermore, in some embodiments, the electronic processor 205 may also update a different metadata field of the selected image study indicating a reason that the selected image study was not processed by the AI system 110 (for example, the AI system's queue is full, manual review is needed, an implant was identified in one of the images, or the like). This information can be used (for example, by the workflow application 225) to manually or automatically assign the image study to a destination for review. Accordingly, using the workflow application 225, an image study can be quickly captured or claimed from a review pool shared by radiologists and the AI system 110 to prevent duplication reviews but can be quickly released when needed for subsequent claiming when the image study cannot be processed by an AI system 110.

In some embodiments, the electronic processor 205 is configured to assign the selected image study to a manual reviewer when the image study cannot be processed by the AI system 110. For example, when the selected image study contains implants or other structures that cannot be read by the AI system 110, the workflow application 225 may be configured to automatically assign the image study to a manual reviewer, such as by updating the workflow status or a field (such as a comments field) indicating that manual review is needed. This workflow status or field may be used to prevent the image study from being claimed by a different AI system (or the same AI system in a situation where the same study was subsequently selected by the workflow application 225). In some embodiments, the workflow application 225 can also assign the image study to a specific manual reviewer (such as a specific physician or radiologist or group of radiologist specialists) to make sure the image study is routed to the most appropriate destination. For example, in some embodiments, the rules applied by the workflow application 225 may define one or more experts who handle image studies with predetermined characteristics and the workflow application 225 may use this information to automatically assign the selected image study to the expert for processing. A priority associated with the image study may also be assigned or updated based on the results of applying the rules. For example, when an image study is identified as not being normal through application of one or more rules as defined above, the image study may be assigned a high priority for reading by a physician to reduce delay in receiving a diagnosis. In some embodiments, the priority may also be used to automatically schedule additional imaging or tests for a patient. Accordingly, by applying the rules, an image study may be quickly and efficiently identified where either an expedited analysis or further imaging or testing is recommended, and this information can be used to quickly schedule or obtain this further imaging or testing, especially when the patient is still present at the imaging facility.

Alternatively, when the selected image study is applicable for processing by the AI system 110 (at block 320), the electronic processor 205 instructs the AI system 110 to process the selected image study (at block 325). In some embodiments, the electronic processor 205 instructs the AI system 110 to process the image study by adding the selected image study to the queue of the AI system 110 for processing. The electronic processor 205 may also be configured to assign or update a workflow status of the selected image study to indicate that the AI system 110 has claimed and is processing the image study. For example, the electronic processor 205 may update the workflow status of the selected image study to "Claimed for Reading by AI System" or a similar workflow status indicating that the AI system 110 is processing the image study.

In some embodiments, the AI system 110 is configured to process the selected image study by preparing at least a partial report for the selected image study (at block 330). For example, the AI system 110 may perform analytics on one or more images included in the selected image study to performs a "read" of these images to determine a diagnosis, note image similarities, take measurements of anatomical structures in images, and otherwise perform analyses on the images in the selected image study in a similar manner to a human reviewer. The AI system 110 may be further configured to automatically populate fields of an electronic report form based upon the findings from the analytics performed during the read of the selected image. Outputs generated by the AI system 110 may be stored in the PACS or a separate system and may be made available to one or more users, such as a radiologist who may review the output for accuracy. Accordingly, an AI system 110 may be configured to create a final report or diagnosis for an image study or prepare an intermediary or preliminary report or diagnosis, which can be manually reviewed by a radiologist or other type of user. During processing of the selected image study with the AI system 110, the workflow status of the image study can be updated at various times to provide insight to other systems and users of the status of the processing. As noted above, manual reviewers may use this information to track when processing an AI system 110 will be complete to perform one or more manual actions based on the output from the AI system 110. The triggering of workflow status updates can be configured or varied as needed to provide users or components of the system 100 with an appropriate level of detail regarding the status of an image study.

In some embodiments, the PACS is a third-party PACS not developed by the same manufacturer as the system 100. In these embodiments, the system 100 may not be able to directly change with the workflow status of image studies. Therefore, in these situations, the system 100 may be configured to access the image study to check the workflow status of the image study (for example, the image study included in a worklist stored in the PACS) to determine whether a radiologist or other reader has opened the study for reading (commonly known as "locking" a study for reading). When the study is locked for reading, the system 100 will not process the study. Furthermore, after the AI system 110 processes the study, the system 100 may be configured to check the worklist of the third-party PACS before exporting any outputs (for example, a partial report) to determine whether a manual reviewer has since claimed the study. When a manual reviewer has claimed the study, the system 100 may not export any outputs (or particular output) to the PACS to avoid a double read of the study.

In further embodiments, the system 100 may be configured to communicate workflow status messages to the third-party PACS even when the system 100 cannot directly change the workflow status of the studies stored in the PACS. Because the PACS is a third-party PACS, the PACS may not be able to "translate" or otherwise interpret messages from the system 100 indicating a change in workflow status for a study. Therefore, in these embodiments, the system 100 further includes a workflow status translator that is configured to interpret messages from the system 100 into a format compatible with the PACS. For example, the workflow status translator may include a proprietary application programming interface (API) of the third-party PACS that is accessible by the system 100, which allows the workflow status to be translated into a status that is compatible with the PACS.

The workflow status translator may also include a Health Level Seven (HL7) module configured to communicate using the HL7 standard. For example, the workflow status translator may be configured to take a workflow status update message from the system 100 and create an HL7 order message (HL7 ORM), which is then sent to the third-party PACS to indicate a change to the image study workflow status. This change could be indicated by a text or numeric value or by assigning the study to the system 100, which may be represented by a value for a reviewer field of the image study, such as "AI-READER." In embodiments where the study is assigned via an HL7 ORM message, an original manual reviewer may be retained as a second value for a reviewer field or as a value in a secondary reader filed so that, in case the study cannot be read by the AI system 110, or when there is a reading error by the AI system 110, the original manual reviewer can be re-assigned to the study.

In some embodiments, the workflow status translator is configured to send an HL7 ORM message to the third-party PACS to assign an image study to a reading pool accessible by the system 100 and may further assign the image study from the reading pool to the system 100. When the system 100 claims the study for reading from the reading pool or when the study is assigned to the system 100 but the reading by the system 100 is cancelled or rejected, the system 100 may send an HL7 order update (ORU) message to clear the system 100 from a reviewer field of the study.

The workflow status translator may also be configured to send an HL7 ORU to the PACS to indicate that the system 100 has created a preliminary (PRELIM) or hold (HOLD) report for an image study. In these embodiments, the system 100 may create a PRELIM or HOLD report with a status indicating that the system 100 is reviewing the image study and that the system 100 will create a second report containing more details after the review is created.

In some embodiments the workflow status translator is configured to use the Integrating the Healthcare Enterprise—Post Processing Workflow (IRE PPFW). This workflow is used by some 3D workstations where there is an option to set a status based on IRE Creator Procedure Step in Progress (IRE RAD 20), which puts the study on hold in the PACS worklist. The workflow status translator then sends an IHE Creator Complete (ME RAD-21) message when the AI system 110 finishes reviewing the study or when the study is cancelled for review (for example, for a failure to read by the AI system 110). The workflow status translator may also be configured to send additional DICOM Modality Performed Procedure Steps (MPPS) to the PACS.

In other embodiments, the workflow status translator is configured to use a text field in a DICOM Structured Reporting (SR) document to indicate workflow status to the third-party PACS. In particular, the workflow status translator may use a text field to indicate claiming of a study by the system 100.

In some embodiments, the system 100 is configured to intercept image studies after the studies are created (for example, at an imaging modality device) but before they are added to the PACS. The system 100 performs processing (such as steps similar to the method 300 described above) to determine whether the studies can be processed by the AI system 110. When a study included in the studies cannot be processed, the study is forwarded to the PACS by the system 100. When a study included in the studies can be processed by the AI system 110, the study is held by the system 100 and processed. After processing is completed, the study and any reports or other digital artifacts created during processing are forwarded to the PACS along with a workflow status indicating the study was already processed. If, at any point, the processing of the study fails, the study may be (immediately) forwarded to the PACS with no digital artifacts.

Thus, embodiments described herein provide methods and systems for selectively processing image studies using an artificial intelligence system. Although embodiments have been described herein in terms of medical images, similar techniques can be applied to other data processing applications, including processing images or data outside of the healthcare industry. For example, when an AI system is available for performing data processing in place of other forms of processing (for example, manual processing or computerized processing), the systems and methods described herein can be used to make efficient use of computer and other resources. Various features and advantages of the invention are set forth in the following claims.

What is claimed is:

1. A system for selectively processing image studies with an artificial intelligence system, the system comprising:
   a non-transitory computer-readable medium storing a plurality of inclusion rules, the plurality of inclusion rules related to an applicability of an image study for processing by the artificial intelligence system; and
   an electronic processor configured to
      access a plurality of image studies awaiting review;
      select one of the plurality of image studies and update a workflow status associated with the selected one of the plurality of image studies to a first status indicating that the one of the plurality of image studies has been claimed for review by the artificial intelligence system;
      apply at least one of the plurality of inclusion rules to the selected one of the plurality of image studies to determine whether the selected one of the plurality of image studies is applicable for processing by the artificial intelligence system;
      in response to determining the selected one of the plurality of image studies is applicable for processing by the artificial intelligence system based on the at least one of the plurality of inclusion rules, process the image study with the artificial intelligence system; and
      in response to determining the selected one of the plurality of image studies is not applicable for processing by the artificial intelligence system based on the at least one of the plurality of inclusion rules, update the workflow status associated with the selected one of the plurality of image studies to a second status to make the selected one of the plurality of images studies available for claiming by a manual reviewer or another artificial intelligence system.

2. The system of claim 1, wherein the electronic processor is further configured to apply at least one of a plurality of exclusion rules to the selected one of the plurality of image studies to further determine whether the selected one of the plurality of image studies is applicable for processing by the artificial intelligence system.

3. The system of claim 1, wherein the electronic processor is configured to process the image study with the artificial intelligence system by adding the selected one of the plurality of image studies to a queue of the artificial intelligence system.

4. The system of claim 3, wherein the plurality of inclusion rules includes at least one rule using a state of the queue of the artificial intelligence to determine whether the selected one of the plurality of image studies is applicable for processing by the artificial intelligence system.

5. The system of claim 1, wherein the plurality of inclusion rules includes at least one rule determining whether the selected one of the plurality of images studies is normal to determine whether the selected one of the plurality of image studies is applicable for processing by the artificial intelligence system.

6. The system of claim 1, wherein the plurality of inclusion rules includes at least one rule determining whether the selected one of the plurality of images studies is associated with a predetermined imaging modality to determine whether the selected one of the plurality of image studies is applicable for processing by the artificial intelligence system.

7. The system of claim 1, wherein the plurality of inclusion rules includes at least one rule determining whether the selected one of the plurality of image studies includes at least a predetermined number of images or types of images to determine whether the selected one of the plurality of image studies is applicable for processing by the artificial intelligence system.

8. The system of claim 1, wherein the plurality of inclusion rules includes at least one rule determining whether the selected one of the plurality of image studies includes an image of a predetermined anatomical structure to determine whether the selected one of the plurality of image studies is applicable for processing by the artificial intelligence system.

9. A method for selectively processing image studies with an artificial intelligence system, the method comprising:
   accessing a plurality of image studies awaiting review;
   selecting one of the plurality of image studies and updating the workflow status associated with the selected one of the plurality of image studies to a first status indicating that the one of the plurality of image studies has been claimed for review by the artificial intelligence system;
   applying, with an electronic processor, at least one of a plurality of exclusion rules to the selected one of the plurality of image studies to determine whether the selected one of the plurality of image studies is applicable for processing by an artificial intelligence system;
   in response to determining the selected one of the plurality of image studies is applicable for processing by the artificial intelligence system based on the at least one of the plurality of exclusion rules, processing the image study with the artificial intelligence system; and
   in response to determining the selected one of the plurality of image studies is not applicable for processing by the artificial intelligence system based on the at least one of the plurality of exclusion rules, updating the workflow status associated with the selected one of the plurality of image studies to a second status to make the selected one of the plurality of images studies available for claiming by a manual reviewer or another artificial intelligence system.

10. The method of claim 9, further comprising applying, with the electronic processor, at least one of a plurality of inclusion rules in addition to the at least one of the plurality of exclusion rules to the selected one of the plurality of image studies to determine whether the selected one of the plurality of image studies is applicable for processing by the artificial intelligence system.

11. The method of claim 9, further comprising returning, with the electronic processor, the selected one of the plurality of image studies to a review pool for claiming by the manual reviewer or another artificial intelligence system when the selected one of the plurality of image studies is not applicable for processing by the artificial intelligence system.

12. The method of claim 9, further comprising assigning, with the electronic processor, the selected one of the plurality of image studies to the manual reviewer when the selected one of the plurality of image studies is not applicable for processing by the artificial intelligence system.

13. The method of claim 9, wherein the selected one of the plurality of image studies further includes an original reviewer.

14. The method of claim 13, further comprising claiming, with the electronic processor, the selected one of the plurality of image studies for processing by the artificial intelligence system from the original reviewer.

15. The method of claim 13, further comprising re-assigning, with the electronic processor, the selected one of the plurality of image studies to the original reviewer when the selected one of the plurality of image studies is not applicable for processing by the artificial intelligence system.

16. The method of claim 9, wherein the exclusion rules include at least rule selected from the group of rules consisting of rejecting image studies that include image artifacts, rejecting image studies when there are patient positioning errors in images, rejecting image studies when the artificial intelligence system is not trained to analyze images within the image studies, rejecting image studies when there is incomplete data or corrupted data, rejecting image studies when any images contain unrecognized anatomical bodies, and rejecting image studies when contrast was not used.

17. The method of claim 9, wherein applying the exclusion rules includes performing analytics on the selected one of the plurality of image studies.

18. A non-transitory, computer-readable medium comprising instructions that, when executed by an electronic processor, perform a set of functions, the set of functions comprising:
   accessing a plurality of image studies awaiting review;
   selecting one of the plurality of image studies and updating the workflow status associated with the selected one of the plurality of image studies to a first status;
   applying at least one of a plurality of inclusion rules and at least one of a plurality of exclusion rules to the selected one of the plurality of image studies to determine whether the selected one of the plurality of image studies is applicable for processing by the artificial intelligence system;
   in response to determining the selected one of the plurality of image studies is applicable for processing by the artificial intelligence system based on the at least one of the plurality of inclusion rules and the at least one of the plurality of exclusion rules, processing the image study with the artificial intelligence system; and
   in response to determining the selected one of the plurality of image studies is not applicable for processing by the artificial intelligence system based on the at least one of the plurality of inclusion rules and the at least one of the plurality of exclusion rules, updating the workflow status associated with the selected one of the plurality of image studies to a second status to make the selected one of the plurality of images studies available for claiming by a manual reviewer or another artificial intelligence system.

19. The non-transitory, computer-readable medium of claim 18, wherein the set of functions further comprises
   assigning a value to a field associated with the selected one of the plurality of image studies indicating a reasoning for the selected one of the plurality of image studies not being applicable for processing by the artificial intelligence system.

20. The non-transitory, computer-readable medium of claim 18, wherein the plurality of image studies only includes image studies that have not been reviewed or that are not currently under review by a manual reviewer or a separate artificial intelligence system.

\* \* \* \* \*